US008053210B2

(12) United States Patent
Dunkelberg

(10) Patent No.: US 8,053,210 B2
(45) Date of Patent: *Nov. 8, 2011

(54) METHOD FOR TESTING A STERILIZATION PACKAGING UNIT FOR ITS EFFICACY AGAINST RECONTAMINATION

(76) Inventor: Hartmut Dunkelberg, Bad Sooden-Allendorf (DE)

( * ) Notice: Subject to any disclaimer, the term of this patent is extended or adjusted under 35 U.S.C. 154(b) by 336 days.

This patent is subject to a terminal disclaimer.

(21) Appl. No.: 10/508,507

(22) PCT Filed: Mar. 19, 2003

(86) PCT No.: PCT/EP03/02843
§ 371 (c)(1),
(2), (4) Date: Apr. 27, 2005

(87) PCT Pub. No.: WO03/080129
PCT Pub. Date: Oct. 2, 2003

(65) Prior Publication Data
US 2005/0191750 A1    Sep. 1, 2005

(30) Foreign Application Priority Data

Mar. 26, 2002    (DE) .................................. 102 13 361

(51) Int. Cl.
*C12Q 1/22* (2006.01)
*B65B 55/02* (2006.01)
*G01N 31/00* (2006.01)

(52) U.S. Cl. ................................. 435/31; 53/425; 436/1

(58) Field of Classification Search ......................... None
See application file for complete search history.

(56) References Cited

U.S. PATENT DOCUMENTS

| 4,596,773 | A | | 6/1986 | Wheeler, Jr. | |
|---|---|---|---|---|---|
| 4,925,789 | A | * | 5/1990 | Edberg | 435/38 |
| 5,167,923 | A | | 12/1992 | Van Iperen | |
| 5,344,017 | A | | 9/1994 | Wittrock | |
| 5,863,496 | A | * | 1/1999 | McElhany | 422/22 |
| 5,922,592 | A | | 7/1999 | Tautvydas | 435/287.4 |
| 5,955,296 | A | | 9/1999 | Roll | 435/31 |
| 2002/0022246 | A1 | | 2/2002 | Lin et al. | |

FOREIGN PATENT DOCUMENTS

| DE | 100 06 767 A1 | 2/2000 |
|---|---|---|
| GB | 2186974 A | 8/1987 |
| WO | WO 01/13964 A1 | 3/2001 |

OTHER PUBLICATIONS

Dunkelberg et al. A New Method for Testing TEH Effectiveness of the Microbial Barrier Properties of Packaging Materials; Biomedizinische Technik, vol. 47 (11) (2002) pp. 290-293 (English Translation).*
BD BBL Prepared Sterile Pack Plates Trypticase Soy Agar, Sterile Pack, Feb. 2000 http://www.bd.com/ds/technicalCenter/inserts/8809381(0200).pdf downloaded Sep. 10, 2008.*
M. J. Akers. Parenteral Quality Control: Sterility, Pyrogen, Particulate and Package Integrity Testing; Second Edition, (1994), Chapter 4, pp. 247-299.*
European Standard, EN 556-1, Sterilization of medical devices—Requirements for medical devices to be designated 'STERILE', pp. 1-6, Oct. 2001.
The Society for Healthcare Epidemiology of America 13th Annual Scientific Meeting, Meeting information, Hartmut Dunkelberg, MD, Bjorn Zietz, MD, and Silke Wedekind, Preliminary Results for a New Final Package Test to Assess the Quality of Sterile Package Systems, pp. 1 and 101, Section 214, Monday, Apr. 7, 2003.
Unpublished U.S. Application—Dunkelberg, U.S. Appl. No. 10/556,550; International filed May 13, 2003 (PCT/EP03/05111).
Single or Multiple Wrapping of Medical Devices: Procedure Assessment Through Research Zentr Steril 7. Jahrgang, 1999; pp. 292-303.
Hygienic-Microbiological and Technical Testing of Steriliser Container Systems Zentr Steril 7. Jahrgang, 1999; pp. 154-162.
Verpackungsmaterialien und-systeme fur zu sterilisierende Medizinprodukte Europaische Norm European Standard Norme Europeenne Feb. 1997, pp. 1-12 .
Sterilgutversorgung; Sterilisationpapier fur Beuter and Schlauchverpackungen Prufung Sterilization; sterile supply; sterilization paper for bags and tube packings, test Jan. 1987; pp. 1-3.
AESCULAP Sterile Containers; Instructions for use/Technical description Dec. 1997; pp. 1-4.
American Society for Testing and Materials F 1608-00 "Standard Test Method for Microbial Ranking of Porous Packaging Materials (Exposure Chamber Method)" pp. 1-9, Jun. 2000.
AESCULAP Basic version of Sterile Containers B. Braun Melsungen AG http://www.bbraun.com/index.cfm?uuid=97E644D8B349489E89 Apr. 11, 2004; one sheet.

* cited by examiner

Primary Examiner — Rebecca Prouty
Assistant Examiner — Paul Martin
(74) Attorney, Agent, or Firm — Ballard Spahr LLP

(57) ABSTRACT

The invention relates to a method for testing a sterilization packaging unit provided for sterilization of objects to be sterilized, in particular medical objects to be sterilized, for its efficacy against microbial recontamination of the sterilized objects after they have been sterilized. In accordance with the invention the packaging unit is charged with nutrient medium, subjected to a sterilization process and then stored for a period of time under ambient conditions. The packaging unit is then kept under conditions in which microbes multiply for cultivation of microbes which are present in or on the nutrient medium. The packaging unit is then opened and microbes, which have multiplied in or on the nutrient medium, are observed. The method permits the efficacy of the packaging unit with respect to its recontamination protection to be tested easily and reliably.

21 Claims, No Drawings

METHOD FOR TESTING A STERILIZATION PACKAGING UNIT FOR ITS EFFICACY AGAINST RECONTAMINATION

The invention relates to a method for testing a sterilization packaging unit provided for sterilization of objects to be sterilized for its efficacy against microbial recontamination of the sterilized objects after they have been sterilized. The objects to be sterilized are, in particular, medical objects to be sterilized.

Many objects must be sterilized before they are used, particularly in the medical field, in order to kill microbes, i.e. living microorganisms, on the objects. Such medical objects to be sterilized can be, for example, instruments, linen or liquids. Depending on the type of objects to be sterilized an appropriate physical or chemical sterilization method is used. In the medical field vapor sterilization methods are predominantly used. These are characterized by a high level of efficacy and environmental compatibility. In vapor sterilization methods sterilization is carried out with confined and saturated steam. The temperature of the steam is for example 121° C. or 134° C. Sterilization is carried out using autoclaves.

Furthermore, microbes can also be killed by high-energy ionizing beams or by a $H_2O_2$-based plasma. Chemical sterilization methods include sterilization by means of ethylene oxide or formaldehyde.

Medical objects to be sterilized are packaged for sterilization. It is possible for this purpose to use container packages, e.g. in the form of a box, paper packages in which the objects to be sterilized are wrapped in a number of layers of paper, and other packages. The package serves to ensure the sterility achieved by the sterilization method until the sterilized objects are used.

The quality requirements for the sterilization method are high. Under WHO guidelines and various European pharmacopoeia, out of 1 000 000 "sterile" products 999 999 must be sterile. The usual sterilization methods are evaluated and standardized with physical-chemical and microbiological parameters. A known and reliable method for testing the efficacy of a sterilization method consists of subjecting a test microbial unit to the sterilization method to be tested, at the same time as the objects to be sterilized. This test microbial unit is formed by a number of microbes which are particularly resistant to the sterilization process and which are enclosed as a unit by a casing. After the sterilization process this test microbial unit is opened under sterile conditions and tested to see if the microbes contained therein are capable of multiplying. If the sterilization process has taken place correctly no multiplication of the test microbes will take place since these test microbes will have been killed by the sterilization. The test microbes therefore represent an indication of the effectiveness of the sterilization method.

There are also quality standards for the packaging material. These generally relate to partial aspects of the packaging unit such as material properties, sealing tightness of closures etc. Suitable methods for testing the efficacy of the package as a whole and/or of a packaging unit in use have not been developed. However, while the sterilization method is regularly checked for efficacy in the manner described, for the period of time between sterilization and the sterilized objects being used, in which recontamination can take place, there are no satisfactory methods, for example of a microbiological type, relating to detecting the efficacy of a sterilization packaging unit in preventing recontamination of the sterilized objects, or with respect to detecting possible recontamination of the sterilized objects.

On the one hand, the so-called microbial barrier of the packaging unit used is a factor in the recontamination of the sterilized objects. This microbial barrier is the ability of the packaging unit to prevent the entry of microorganisms. On the other hand, various external influences such as the type of storage or transportation and mechanical stressing on the packaged sterilized objects and ambient influences such as air flow, microbial content of the air and fluctuations in air pressure are factors in recontamination.

A known method of testing the microbial barrier quality of partial components of a container package consists of generating negative pressure in the container via orifices provided in a cover of the container (EN 868-1, Appendix G). By means of this negative pressure the tightness of a seal between the cover and the container body can be tested. However, this is merely one specific physical method for packages which are in the form of containers, and this method also only concerns the seal between the body and the cover but not the microbial barrier of the vapor orifices such as filters and valves. Furthermore, ambient influences, e.g. microbial content of the air, are not included in this testing method. This method can therefore give no reliable evidence as to the extent to which recontamination of sterilized objects in the packaging unit must be expected.

Furthermore, there is a microbiological DIN testing method (DIN 58953, Part 6) which is provided to test sterilization paper. In this method a microbial penetration testing unit in the form of a glass laboratory flask is closed with the sterilization paper to be tested and is tested to see whether, by cooling the air in the microbial penetration unit, an air flow passes into the glass laboratory flask and carries particles containing microbes through the sterilization paper when the paper has been charged with spore earth prior to cooling. Provision is made to heat the glass laboratory flask to 50° C. and to cool it to 10° C. repeatedly and consecutively. Spores which may enter the glass laboratory flask through the sterilization paper are detected and evaluated by microbiological means using incubation of the glass laboratory flask containing nutrient medium. This testing method, however, does not relate to a packaging unit as a whole but only to paper which is used as a packaging material. This is purely a material test in which, apart from the application of spore earth, no further ambient influences are included.

It is also known to test some of the sterilized objects for recontamination after a certain period of time by means of random sampling. However, a disadvantage of this is the fact that to do this the packaging unit needs to be opened and, during the test itself, microbes can reach the object being tested so that the result of the test can thereby be rendered erroneous. However, this method is not practicable for hospital use so that it is not routinely used in hospitals.

From the publication of by de Bruijn, A. C. P. and Kastelein, J., Einfach-oder Mehrfach-Verpackung von Medizinprodukten: Verfahrensbewertung durch Forschung, Zentralsterilsation; 1999; 7 (5): 292-303 a method is known with which the filtering effect of a package with respect to an aerosol consisting of 1.0 μm latex particles is determined by means of a particle counter (cf. loc. cit. 3., page 297, para. 1). The known method is not intended, and is not suitable for testing packages in the form in which they are used in order to determine their capability to maintain sterility under hospital practice conditions. In particular, the method is not based on the determination of the relevant end point, namely the detection of microbiological contamination.

From the publication by Junghannβ U., Winterfeld S., Gabele L., Kulow U., Hygienisch-mikrobiologische und technische Überprüfungen von Sterilisier-Containersystemen, Zentralsterilisation 1999; 7 (3): 154-162 a method is known for testing sterilization containers in the form of packaging containers. In this method a test chamber is used into which the containers to be tested can be inserted. Before they are placed in the test chamber the containers were fitted with the associated filters and sterilized. The containers were then provided with solid nutrient media in Petri dishes and closed. A microbe-containing aerosol was introduced into the interior of the test chamber using a spray bottle. By means of connection fittings fitted to the containers to be tested prior to introduction into the test chamber, suction was carried out through the containers to be tested, by means of a hose pump. After the suction the containers were opened again and the solid nutrient medium dishes were removed. These were then incubated to test for microbes on the solid nutrient medium. The colony-forming units (cfu) were then counted.

The known method is not suited to testing an end-usage package, in the form in which it is used in practice, in order to test its barrier efficacy with respect to recontamination. It is rather the case that the containers need to be provided with a suction fitting before being introduced into the known test chamber. Furthermore, after the containers have been in contact with the aerosol in the test chamber, they must be removed from the test chamber and opened in order to remove the solid nutrient medium dishes and to incubate them in a separate apparatus. The container cannot therefore remain in an undisturbed condition until the results of the test are evaluated. External sources of errors can therefore not be ruled out during the test. It is rather the case that the removal of the solid nutrient medium dishes for subsequent incubation is associated with a risk of contamination and therefore with the risk of imprecise measurement.

According to Junghannβ et al. only a difference value for the microbial barrier is determined but no absolute value is obtained. In the known testing arrangement no evidence as to sterility could be obtained because of the non-sterile handling of the solid nutrient medium.

It is therefore the object of the invention to provide a generic method, which is effective and simple to implement, for testing a sterilization packaging unit as a whole with respect to its efficacy against recontamination of the sterilization objects after they have been sterilized.

In the method in accordance with the invention the packaging unit is charged with nutrient medium, subjected to a sterilization process and stored under ambient conditions for a period of time. The packaging unit is then subjected to conditions which promote multiplication of microbes or microorganisms in or on the nutrient medium in order to cultivate living microbes which may be present on or in the nutrient medium. This may be, in particular, incubation, for example in an incubator or incubation chamber. The multiplication conditions include e.g. a temperature suitable for the multiplication of the microbes expected to be present, and a suitable gas atmosphere. This cultivation generally takes place over a preset period of time. The packaging unit is then opened and microbes which have multiplied in or on the nutrient medium are observed. If it is the case that, after the sterilization process, which is assumed to have been carried out correctly or the correct implementation of which has been tested by means of the test microbe indicators described above, contamination of the nutrient medium by entry of microbes into the packaging unit and settlement in or on the nutrient medium has taken place, the microbes have been cultivated as described above. If microbes have been found multiplying in or on the nutrient medium then this is clear evidence that microbes have entered the sterilization packaging unit after the sterilization process. This may be attributable to the fact that the sterilization packaging unit has basic faults or it may also be attributable to the fact that the ambient conditions, such as humidity and the microbial content of the air, were very unfavorable in relation to the avoidance of recontamination.

The method in accordance with the invention is simple to implement and permits extensive testing of a sterilization packaging unit or of a fundamental construction of a sterilization packaging unit with respect to its efficacy against recontamination of the sterilized objects. This test is extensive because, in contrast to the prior art, it does not only test partial functions such as the sealing tightness between the cover and the body of a specific container packaging unit, or the microbial penetration of sterilization paper, but includes the microbial barrier of the whole packaging unit in dependence upon material, shape and construction features, and because the specific ambient conditions which influence the recontamination risk are also included in the test. In particular it is not possible with this testing method to obtain erroneous test results by opening the package.

In order to determine the influence of the ambient conditions on the risk of recontamination it is advantageous to predetermine in the most defined manner possible the ambient conditions and the period of storage of the packaging unit between the sterilization process and the cultivation step.

The packaging unit can be provided with objects to be sterilized as well as with the nutrient medium. If microbes which are capable of multiplying are found in or on the nutrient medium after the cultivation step it must be assumed that the sterilized objects have also been recontaminated in a corresponding manner. If, in contrast, the nutrient medium, in or on which the microbes have very good to optimal living conditions in association with the ambient conditions provided during the cultivation, has no multiplying microbes it can reliably be assumed that the sterilized objects are not recontaminated. The cultivated nutrient medium therefore has an indicator function with respect to recontamination of the sterilized objects. This embodiment of the method in accordance with the invention is therefore clearly superior to the method of testing some of the sterilized objects which uses random sampling and provides little definite evidence. In particular, the test result in accordance with the method of the invention is much less liable to error than the known random sampling test in which contamination of the subject of the test can take place by means of the test process itself.

The sterilization process can take place in particular in the form of vapor sterilization. However, other sterilization methods are also feasible, e.g. sterilization by means of high-energy ionizing beams or specific chemical substances such as ethylene oxide or formaldehyde.

The nutrient medium can be a standard medium or a selective nutrient medium which is particularly adapted to the growth or multiplication of certain microbes. The nutrient medium is preferably a solid nutrient medium so that the packaging unit can be transported in a problem-free manner with the solid nutrient medium therein. In a conventional and favorable manner it is an agar-based solid nutrient medium. In the case of vapor sterilization and use of an agar-based solid nutrient medium a sterilization program should be selected which ensures that, subsequent to the sterilization phase, by the application of a vacuum the still liquid agar cannot boil over because of a delay in boiling.

When using a solid nutrient medium the number of colonies grown on the solid nutrient medium can be determined by counting as a measure of the efficacy of the packaging unit against recontamination. It is therefore also possible to obtain quantitative evidence with respect to the barrier effect of the packaging unit under preset ambient conditions.

The solid nutrient medium can be introduced into a thermostable glass or synthetic material dish. The whole bottom surface of the packaging unit can be covered by such dishes. It is also fundamentally feasible to place the solid nutrient medium directly into a container package if this package has a closed bottom, i.e. in particular if it is not provided with a valve for drainage of condensed water. Insertion of solid nutrient medium in dishes into the packaging unit makes the solid nutrient medium particularly simple to handle. The said covering of the bottom surface of the packaging unit with solid nutrient medium permits a particularly high level of reliability for the method.

If, during the sterilization process, a sterilization method is used which is associated with increasing the temperature of the content of the packaging unit then the packaging unit should be allowed to cool before it is stored for the period of time under the ambient conditions. When using an agar-based solid nutrient medium the packaging unit should cool to below 40° C. since agar is liquid at temperatures higher than 40° C.

The packaging unit can be a container package, a paper package or another type of package. In the case of the paper package it is possible, e.g. for a sterilization screen to be used, on which instruments provided for sterilization are disposed.

Furthermore, provision can be made in accordance with the invention to test a sterilization packaging unit provided to sterilize objects to be sterilized, in particular medical objects to be sterilized, for its efficacy against microbial recontamination of the sterilized objects after they have been sterilized, in dependence upon variable ambient conditions, in that one of the methods described above is applied repeatedly and consecutively, wherein, however, the ambient conditions under which the packaging unit is stored over the period of time are different upon each application of the method. A number of identical samples of one type of packaging unit can be simultaneously subjected to the methods described above which differ only in respect of the ambient conditions.

This method permits the highest possible protection to be achieved against recontamination of sterilized objects located in a certain type of sterilization packaging unit, in that ambient conditions are found which, in association with the sterilization packaging unit, ensure the desired protection against recontamination. In this way it is possible to obtain evidence about the necessary hygienic quality of a chamber in which the packaging unit is stored, or to determine a profile of requirements for such a chamber. By means of the method it is therefore possible to set ambient air hygiene characteristics for parameters such as microbial content of the air, but also characteristics for parameters for transport conditions such as jarring. With this embodiment of the invention the sterilization packaging unit and also the ambient conditions are therefore parameters which should be set corresponding to the higher aim of achieving the highest possible protection against recontamination or a specific level of protection while optimizing the expense. The type of packaging unit and the ambient conditions are set and/or tested in relation to each other.

A test of this extensive type in which requirements for a chamber quality can be determined in dependence upon a particular packaging unit is permitted only by the present invention.

The invention is explained in more detail herein under with the aid of an exemplified embodiment.

EXEMPLIFIED EMBODIMENT

A reusable sterilization container for vapor sterilizers in accordance with EN 285 is to be tested for its efficacy in preventing recontamination of sterilized objects. The container is a container package 596×275×115 mm in size, having a cover which comprises a filter. In preparation for testing the container two open thermostable dishes (size 175×225 mm) each with 300 ml of nutrient medium CASO-agar (Merck) are placed in a screen dish (515×245×60 mm). The charged screen dish is placed into the body of the container and the container is closed by the cover.

The container is then subjected to a sterilization process. A vapor sterilizer (autoclave) is used for this purpose. The sterilization temperature is 121° C., the sterilization time is 15 min. A program for solutions which are to be sterilized is used as the sterilization program. A program such as this has the advantage that the still liquid agar does not boil over because of a delay in boiling.

After the sterilization process the container is either transported and stored under the usual conditions used in practice, or the container is subjected to experimental conditions which are defined with respect to the microbial content of the air, fluctuations in air pressure and transport path. The duration of exposure is selected to have a value in the range of about 1-4 days.

The container which is still closed is then placed into an incubator at 37° C. for 48 hours for cultivation purposes.

After this cultivation, colonies which have grown on the solid nutrient base are counted. These colonies are colony-forming units (cfu), the number of which corresponds to the number of microbes which have penetrated by recontamination. Thus the number of colonies is a measure of the recontamination and therefore of the efficacy of the container as a barrier to ensuring sterility.

The invention claimed is:

1. A method for testing a gas permeable sterilization packaging unit formed wholly of gas permeable material or having at least one gas permeable component, the packaging unit being provided for sterilization of objects to be sterilized for its efficacy against microbial recontamination of the objects after they have been sterilized, the method comprising:
Charging the gas permeable packaging unit with a non-liquid nutrient medium being open to settlement of microbes;
Sterilizing the gas permeable packaging unit;
Storing the gas permeable packaging unit for a period of time under ambient conditions;
Placing the gas permeable packaging unit in an incubator or incubation chamber;
Incubating the gas permeable packaging unit in the incubator or incubation chamber to promote multiplication of microbes expected to be present, by subjecting the gas permeable packaging unit over a preset period of time to a temperature and a gas atmosphere each being favorable for the multiplication of said microbes, in order to cultivate said microbes in case those would be present in or on the nutrient medium due to recontamination after sterilization; and
Observing if microbes multiplied in or on the nutrient medium.

2. A method according to claim 1, wherein said ambient conditions and said period of time under which said gas permeable packaging unit is stored are predetermined.

3. A method according to claim 2, further comprising repeating said method and storing said gas permeable packaging unit under different predetermined ambient conditions for each repetition of said method.

4. A method according to claim 2, further comprising charging said gas permeable packaging unit with said objects prior to sterilizing said gas permeable packaging unit.

5. A method according to claim 2 wherein said gas permeable packaging unit is sterilized by vapor sterilization.

6. A method according to claim 2, wherein said nutrient medium is a selective nutrient medium.

7. A method according to claim 2, wherein said nutrient medium is a solid nutrient medium.

8. A method according to claim 1, including charging said gas permeable packaging unit with said objects prior to sterilizing said gas permeable packaging unit.

9. A method according to claim 8 wherein said gas permeable packaging unit is sterilized by vapor sterilization.

10. A method according to claim 8, wherein said nutrient medium is a selective nutrient medium.

11. A method according to claim 8, wherein the sterilized objects are medical objects.

12. A method according to claim 1, wherein said gas permeable packaging unit is sterilized by vapor sterilization.

13. A method according to claim 1, wherein said nutrient medium is a selective nutrient medium.

14. A method according to claim 1, wherein said nutrient medium is a solid nutrient medium.

15. A method according to claim 14, further comprising measuring the efficacy of the gas permeable packaging unit for preventing contamination by determining the number of microbe colonies grown on said solid nutrient medium, each of said colonies being attributable to a microbe initiating said colonies.

16. A method according to claim 14, further comprising containing said solid nutrient medium in a thermostable dish.

17. A method according to claim 16, further comprising covering a bottom surface of said gas permeable packaging unit with said dishes containing said solid nutrient medium.

18. A method according to claim 14, wherein;

Said solid nutrient medium is an agar-based solid nutrient medium;

Said sterilizing said gas permeable packaging unit involves an increase in its temperature; and Said gas permeable packaging unit is allowed to cool to a temperature below 40° C. after said sterilizing and prior to said storing said gas permeable packaging unit.

19. A method according to claim 1, wherein the sterilized objects are medical objects.

20. A method according to claim 1, wherein said nutrient medium is an agar-based solid nutrient medium.

21. A method according to claim 1, further comprising observing if microbes multiplied in or on the nutrient medium by determining the number of bacteria using a quantitative method.

\* \* \* \* \*